United States Patent
Kenneth

(10) Patent No.: US 8,412,311 B2
(45) Date of Patent: Apr. 2, 2013

(54) FLUOROSCOPY-FREE GUIDEWIRE SYSTEMS AND METHODS

(75) Inventor: J. Chang Kenneth, Cerritos, CA (US)

(73) Assignee: The Regents of the University of California, Oakland, CA (US)

( * ) Notice: Subject to any disclaimer, the term of this patent is extended or adjusted under 35 U.S.C. 154(b) by 1228 days.

(21) Appl. No.: 11/573,220

(22) PCT Filed: Sep. 12, 2005

(86) PCT No.: PCT/US2005/032475
§ 371 (c)(1),
(2), (4) Date: May 17, 2007

(87) PCT Pub. No.: WO2006/031765
PCT Pub. Date: Mar. 23, 2006

(65) Prior Publication Data
US 2008/0071170 A1     Mar. 20, 2008

Related U.S. Application Data

(60) Provisional application No. 60/609,501, filed on Sep. 13, 2004.

(51) Int. Cl.
*A61B 6/00* (2006.01)

(52) U.S. Cl. ... 600/434; 600/104; 600/424; 604/164.13; 606/151

(58) Field of Classification Search ............... 600/424, 600/104, 434; 128/899; 604/164.13; 606/151
See application file for complete search history.

(56) References Cited

U.S. PATENT DOCUMENTS

| | | | |
|---|---|---|---|
| 4,905,698 A | | 3/1990 | Strohl, Jr. et al. |
| 6,785,571 B2 | | 8/2004 | Glossop |
| 7,650,178 B2 * | | 1/2010 | Scheffler ............. 600/424 |
| 7,881,770 B2 * | | 2/2011 | Melkent et al. ........ 600/424 |
| 2003/0055317 A1 | | 3/2003 | Taniguchi et al. |
| 2003/0160721 A1 | | 8/2003 | Gilboa et al. |
| 2004/0097804 A1 | | 5/2004 | Sobe |

OTHER PUBLICATIONS http://www.olympusamerica.com/msg_section/msg_PressDetails.asp?pressNo=314; ScopeguideTM Real-Time Endoscope Positioning System: Fact Sheet: Oct. 2004; Olympus Corporation, Tokyo, Japan; Olympus America Inc. Melville, NY, US, 2 pages.
http://www.wilsoncook.com/infocus_4.html; Triclip Endoscopic Clipping Device; Copyright © 2005 Wilson-Cook Medical, Inc. Winston-Salem, NC, US, 1 page.
http://www.olympus.com.au/servlet/ContentServer?productpage=ProductList&cid=1095366609026&pagename=0lympusMedical%2FPage%2FMPGProducts&context=Endoscopy%2CEndo+Therapy%2CClip+Fixing+Devices&productId=1095265426075&sectionId=1085025989236; Endoscopy/Endo Therapy/Clip Fixing Devices; Copyright © 2004 Olympus Corporation, Tokyo, Japan, 2 pages.
http://www.bostonscientific.com/med_specialty/deviceDetail.jsp?task=tskBasicDevice.jsp&sectionId=4&relId=7,334,335,336&deviceId=16057; Resolution™ Clip; Copyright 2005 Boston Scientific Corporation, Natick, MA, US, 2 pages.

* cited by examiner

*Primary Examiner* — Brian Casler
*Assistant Examiner* — Daniel Huntley
(74) *Attorney, Agent, or Firm* — Shimokaji & Assoc, PC

(57) ABSTRACT

A system (10) includes electromagnetic indicator coils (30) included in surgical devices, examples of surgical devices (20) including guidewires; surgical instruments including dilators, stents, catheters, jejunostomy tubes, and endoscopes; and indicator clips (used for marking a location within patient). An innovative device indicator is attachable to any surgical instrument to convert it to an electromagnetically monitorable instrument. A monitoring unit (50) detects electromagnetic fields from the electromagnetic indicator coils and displays the location and configuration of the electromagnetic indicator coils on a display unit (80). The relative positions and overall configuration of multiple devices—such as guidewires, instruments, and location marker indicator clips—can all be simultaneously electromagnetically monitored with the use of radiology.

14 Claims, 6 Drawing Sheets

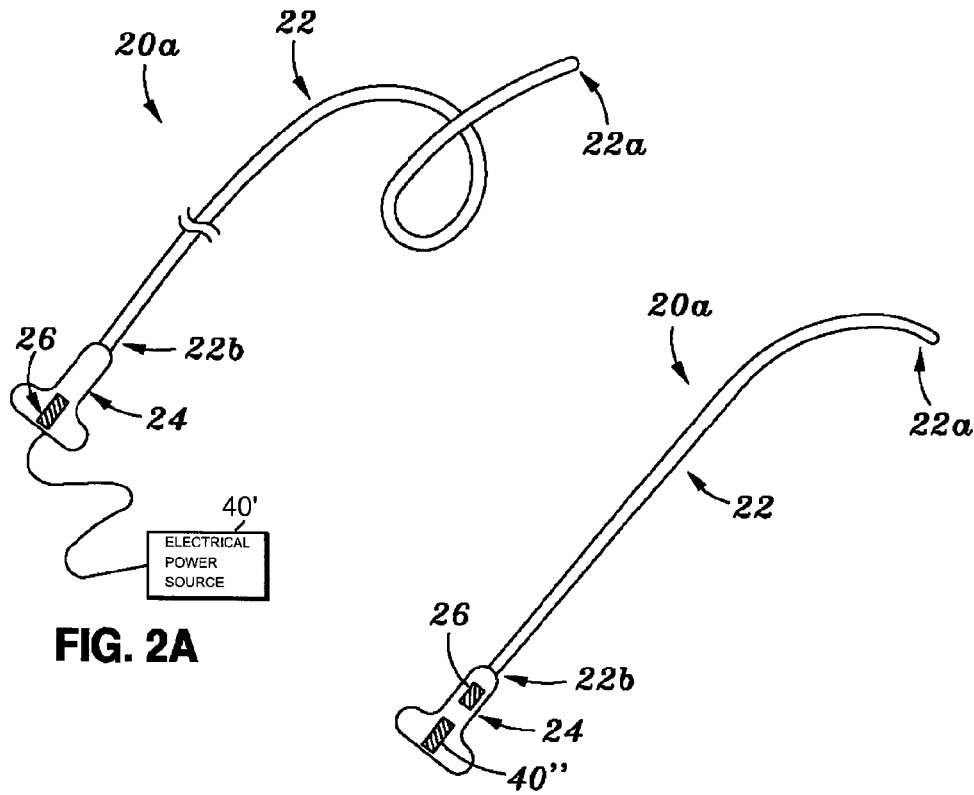
FIG. 2A
FIG. 2B
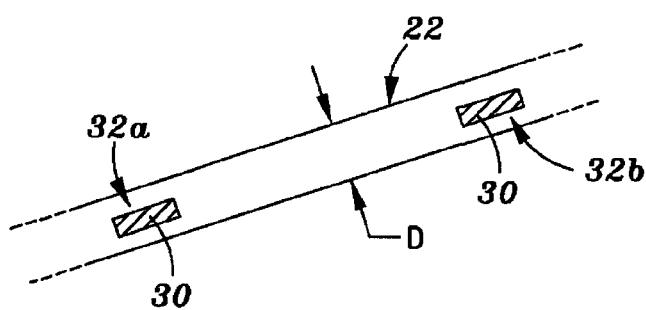
FIG. 3

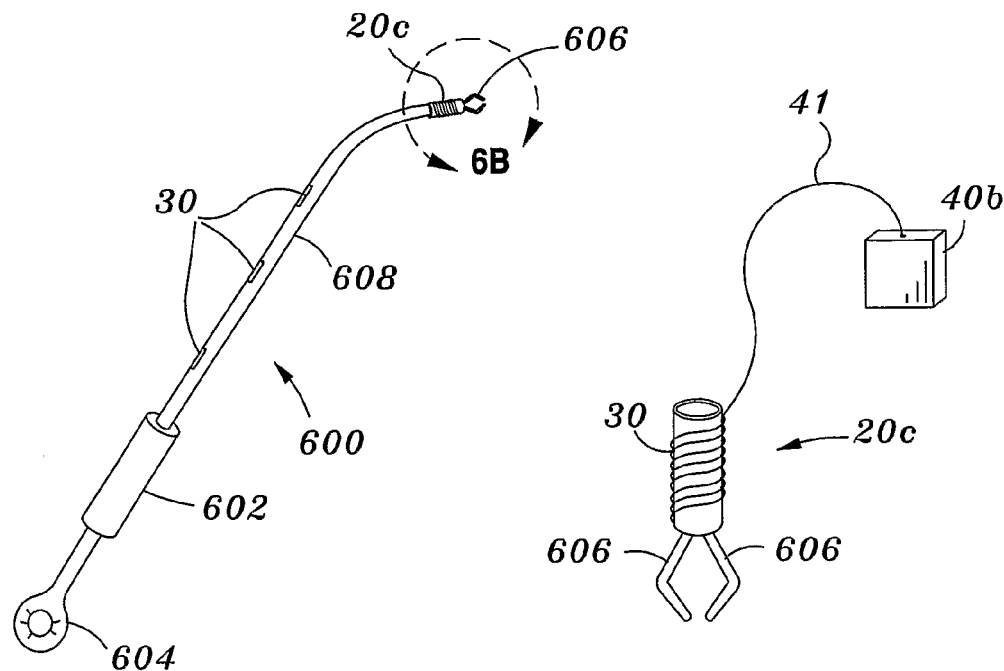
FIG. 6A  FIG. 6B
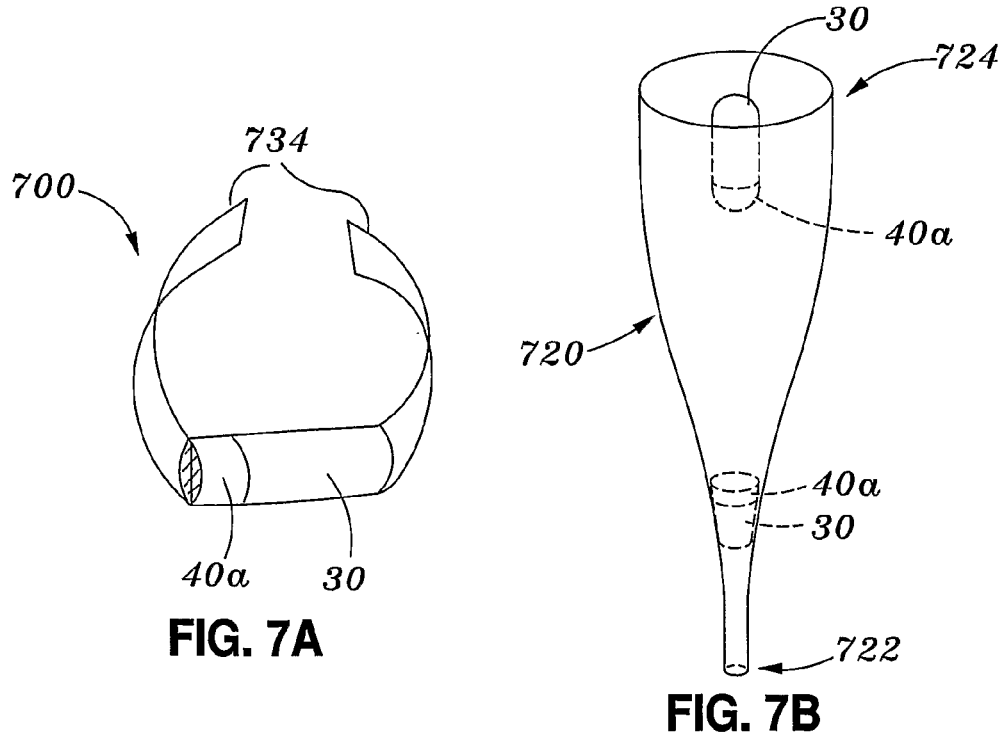
FIG. 7A  FIG. 7B

FLUOROSCOPY-FREE GUIDEWIRE SYSTEMS AND METHODS

CROSS REFERENCE TO RELATED APPLICATIONS

This application claims the benefit of U.S. Provisional Application No. 60/609,501 filed 13 Sep. 2004.

BACKGROUND OF THE INVENTION

The present invention generally relates to surgical procedures and, more particularly, to positioning and monitoring the position and configuration of surgical implements.

Endoscopes are well known in the field of medicine. Endoscopes with a soft insertion unit can be inserted into the lumen of a body cavity to diagnose problems located in a deep region in the body cavity without the necessity of incision and can also be used to guide treatment appliances to a desired location within the body cavity. In the past, medical practitioners have needed to use radio-opaque markers or contrast either in the patient or on the instruments (or both) in order to visualize instrument placement under fluoroscopy. In cases where x-ray exposure under fluoroscopy is contra-indicated or where the scheduling of procedures to occur in radiology is economically or logistically discouraging, alternative measures are needed that can substitute, for example, for injecting contrast into the gastrointestinal (GI) tract in order to "tattoo" a certain area which can be visualized on fluoroscopy; or for indicating the location of existing endoscopes or accessory devices—such as a stent deployment catheter, a Stretta radiofrequency catheter, or a dilator. One such accessory device is a clip that can be used, for example, to hold portions of tissue together. The clip can be inserted into the body cavity using a clip fixing device available, for example, from Olympus Corporation (Tokyo, Japan), Wilson-Cook Medical, Inc, (Winston-Salem, N.C., US), and Boston Scientific Corporation (Natick, Mass., US).

When inserting, for example, an endoscope, a guidewire, or clip fixing device, each of which includes a long flexible tube, it is possible for the tube to bend back on itself or form a loop or enter some other undesirable configuration. An endoscope, for example, typically has a steerable end that can be curved in different directions under the control of the operator and it is useful for the operator to know whether the configuration of the endoscope end is achieving a desired position and whether a position of a treatment appliance—such as a dilator, stent, or clip—relative to the position of the endoscope—for example, in some cases the appliance may be passed through the endoscope—is as desired. In the past fluoroscopy has been used to monitor the configuration of endoscopes. Recently, a colonoscope, which is a particular type of endoscope, known as ScopeGuide™ and marketed by Olympus Corporation, Tokyo, Japan, has electromagnetic coils which allow visualization of the colonoscope configuration on a monitor. A system for detecting the shape of an endoscope using source coils and sense coils via a detection system having a processor included in a control unit is disclosed in U.S. Patent Application Publication No. 20030055317, assigned to Olympus Optical Co., and incorporated by reference.

As can be seen, there is a need for positioning a variety of surgical instruments and monitoring the positions and configurations of those instruments while providing an alternative visualization to that offered by fluoroscopy.

SUMMARY OF THE INVENTION

In one embodiment of the present invention, a system includes an electromagnetic indicator coil included in a surgical device; and a monitoring unit adapted to detect an electromagnetic field from the electromagnetic indicator coil and display the location and configuration of the electromagnetic indicator coil on a display unit.

In another embodiment of the present invention, a guidewire includes a guidewire shaft; and a plurality of electromagnetic coils spaced longitudinally along the guidewire shaft. Each of the plurality of electromagnetic coils is adapted for generating a corresponding one of a plurality of electromagnetic fields. The plurality of electromagnetic fields jointly defines a configuration of the guidewire shaft.

In still another embodiment of the present invention, a surgical instrument includes at least one electromagnetic coil adapted for generating a corresponding electromagnetic field, which defines a configuration of the surgical instrument.

In yet another embodiment of the present invention, an indicator clip includes fingers for gripping tissue and at least one electromagnetic coil adapted for generating an electromagnetic field detectable by a monitoring system.

In a further embodiment of the present invention, a guidewire system includes a guidewire having a guidewire shaft; multiple electromagnetic coils adapted for generating corresponding electromagnetic fields; a detection unit for generating location data indicative of a relative location of each of the magnetic coils; a data processing unit for transforming the location data into image data representing a configuration of the guidewire shaft; and a display unit for displaying an image representing the configuration of the guidewire shaft.

In a still further embodiment of the present invention, a method is disclosed for monitoring a configuration of a guidewire, in which the guidewire includes a guidewire shaft and multiple electromagnetic coils spaced longitudinally along the shaft; the method including: a) generating an electromagnetic field from each of the electromagnetic coils; b) electromagnetically detecting the electromagnetic fields; c) generating location data indicative of a relative location of each of the magnetic coils; d) transforming the location data into image data representing a configuration of the guidewire shaft; and e) via a display unit, displaying an image representing the configuration of the guidewire shaft.

In a yet further embodiment of the present invention, a surgical method includes: electromagnetically monitoring a guidewire during insertion of the guidewire into a lumen of a body cavity of a patient; using the guidewire to guide a surgical device having an electromagnetic indicator coil; and electromagnetically monitoring the surgical device and the guidewire while guiding the surgical device.

These and other features, aspects and advantages of the present invention will become better understood with reference to the following drawings, description and claims.

BRIEF DESCRIPTION OF THE DRAWINGS

FIG. 2A is a schematic illustration of a guidewire in a looped configuration, in accordance with an embodiment of the present invention;

FIG. 2B is a schematic illustration of a guidewire in a curved configuration, in accordance with an embodiment of the present invention;

FIG. 3 is an enlarged view of a portion of a guidewire shaft showing a plurality of spaced apart coils, according to an embodiment of the present invention;

FIG. 6A is a schematic diagram of an instrument used for placing an indicator clip, according to one embodiment of the present invention;

FIG. 6B is a schematic diagram of the indicator clip of FIG. 6A after detachment from the instrument used for placing the indicator clip;

FIG. 7 is a schematic diagram for one example of an instrument-mountable indicator, according to one embodiment of the present invention.

DETAILED DESCRIPTION OF THE INVENTION

Figure 1:
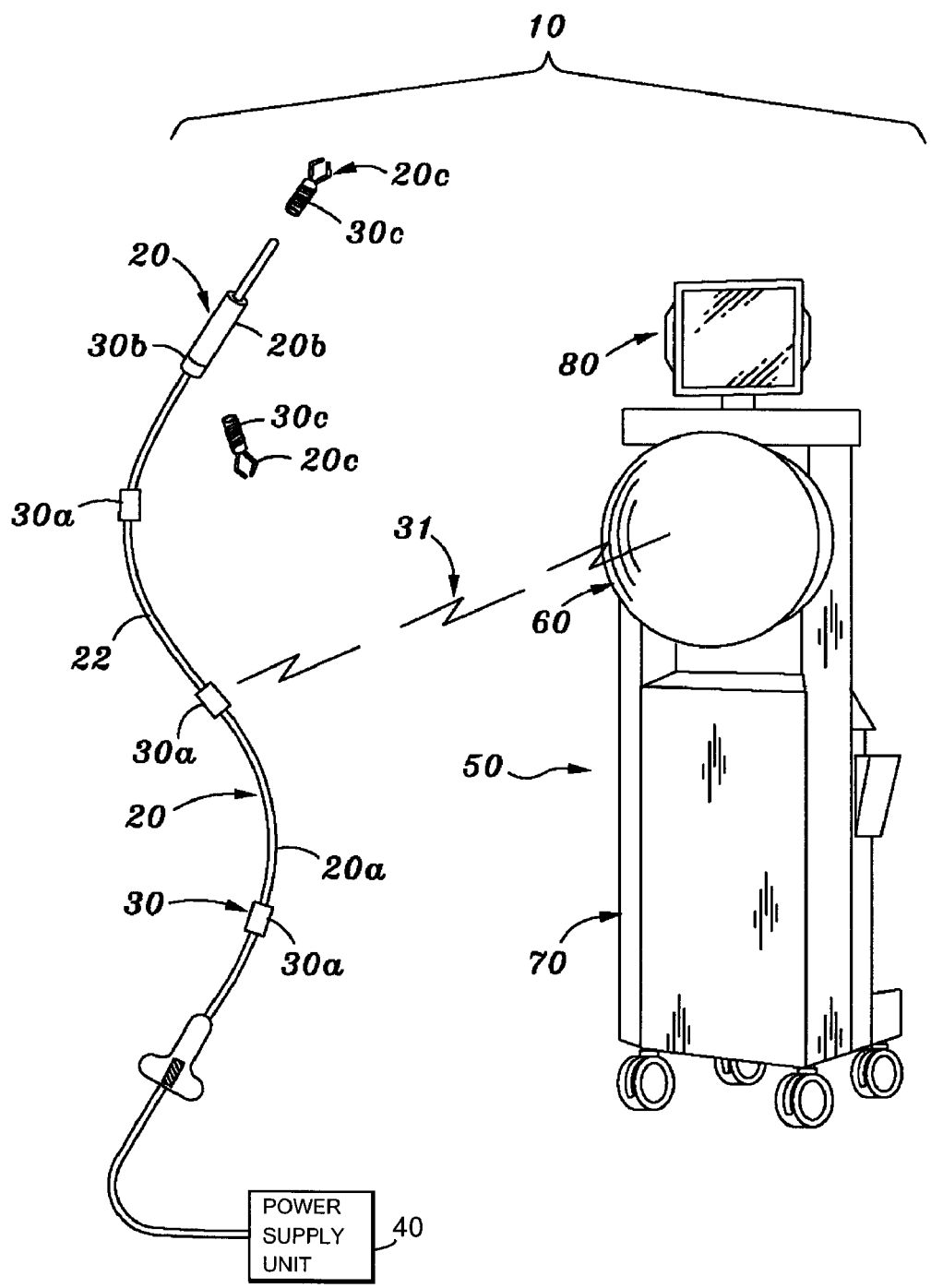
FIG. 1 is a schematic illustration of a surgical instrument monitoring system, according to one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides for monitoring the configuration and positioning of various surgical instruments relative to each other including guidewires, catheters, endoscopes, stents, dilators, and clips that, for example, may be clipped onto a patient's tissue at selective locations. An embodiment of the present invention may be used to monitor guidewire shaft configuration by displaying an image of the guidewire shaft on a display unit. For example, one embodiment of the present invention may be used for monitoring guidewire shaft configuration during an endoscopic procedure, wherein the guidewire shaft may be manipulated with respect to tissues or organs of a patient's body. In addition, embodiments of the present invention provide more general applicability, for example, by allowing the monitoring of surgical instruments other than endoscopes (to which prior art electromagnetic monitoring of surgical instruments has been limited).

The present invention also provides a guidewire, which in contrast to conventional guidewires does not require fluoroscopy to visualize—but instead uses electromagnetic signals emitted from source (indicator) coils on the wire itself—which is detected and displayed on the monitor—so that a configuration of the guidewire shaft may be defined by the plurality of electromagnetic fields. In further contrast to prior designs, a configuration of the guidewire shaft of the present invention may be visualized on a display unit in real time during a procedure while the guidewire shaft is inserted in a patient's body. Unlike the present invention, visualization of conventional guidewires has typically used fluoroscopy, which not only requires bulky equipment, but also may expose both the patient and the surgical team to X-ray irradiation.

Also provided by the present invention is an indicator clip that differs from past designs in that, for example, instead of injecting contrast into the GI tract in order to "tattoo" a certain area which can be visualized on fluoroscopy, the indicator clip can be placed using a clip fixing device to insert the clip through the lumen of the GI tract, and attached to the patient by gripping a portion of the patient's tissue, in order to be placed along the inside of the gastrointestinal tract for marking purposes using electromagnetic field sensing instead of fluoroscopy. The device indicator of the present invention similarly differs from past designs in that devices previously were not marked for radiographic contrast under fluoroscopy, whereas the electromagnetic device indicator provides electromagnetic location information for a device to which it may be attached. Embodiments of the present invention provide an electromagnetic way of marking tissue, devices and guidewires relative to each other.

For example, in one embodiment of the present invention, an indicator clip may be monitored, wherein the indicator clip emits an electromagnetic field and the clip can be placed along the inside of the gastrointestinal tract for marking purposes, e.g., marking the position of an alternated anatomy. In another embodiment, an electromagnetic device indicator may be monitored and is an accessory which can be placed onto any existing endoscope or accessory device. A small profile electromagnetic device indicator can be taped, strapped, or fastened to an endoscope or device (such as a stent deployment catheter or a Stretta radiofrequency catheter, for example). One or several device indicators could be used to locate the positions of multiple devices. Each indicator would individually be seen on a detector monitor. The indicator clip and the electromagnetic device indicator could be used separately or together. For example, for endoscopic stent placement: an electromagnetic indicator clip may be placed at the proximal and distal ends of an esophageal tumor. Then the stent deployment device may have several device indicators which allow for stent deployment at the proper position relative to the indicator clips and the tumor. As another example, for esophageal dilation, the dilator could have two device indicators attached or even embedded into the dilator itself.

FIG. 1 schematically represents a monitoring system 10, according to one embodiment of the invention. Monitoring system 10 may include a surgical device 20—such as guidewire 20a, surgical instrument 20b (e.g., stent or dilator), or indicator clip 20c—having one or more electromagnetic indicator coils 30, also referred to as source coils (also see, for example, FIG. 3). In the case of guidewire 20a, the plurality of electromagnetic indicator coils 30 may be spaced—for example, every 1.0 centimeter (cm)—longitudinally along a guidewire shaft 22 (see also, e.g., FIGS. 2A-2B and FIG. 3). The plurality of electromagnetic indicator coils 30 may be adapted for generating a corresponding plurality of electromagnetic fields 31.

Monitoring system 10 may further comprise a power supply unit 40 for providing electrical power to surgical device 20. Power supply unit 40 may allow passage of an electric current through the plurality of electromagnetic indicator coils 30 for generating the corresponding plurality of electromagnetic fields 31. In some embodiments, power supply unit 40 may comprise a battery (see FIG. 2B), or other suitable source of electric current.

Monitoring system 10 may still further comprise a monitoring unit 50, which may include a detection unit 60. Detection unit 60 may be adapted for generating location data indicative of a relative location of each of the plurality of electromagnetic indicator coils 30. The relative location of each of the plurality of electromagnetic indicator coils 30 may be indicated by a relative location of each of the corresponding plurality of electromagnetic fields 31. As an example, detection unit 60 may include a plurality of detection coils (not shown) for detecting a location of each of the plurality of electromagnetic indicator coils 30. Monitoring unit 50 may further include a data processing unit 70 for transforming the location data into image data, wherein the image data may represent the configuration of the guidewire shaft 22 or locations and orientations of any of the surgical devices 20. Data processing unit 70 may comprise a microprocessor or central processing unit (CPU), or a computer, together with suitable software for performing algorithms for transforming the location data into image data. Monitoring unit 50 may still further include a display unit 80 for displaying an image showing the configuration of guidewire shaft 22 or locations and orientations of any of the surgical devices 20. As an example, the configuration of guidewire shaft 22 may be curved (see FIG. 2B) or looped (FIG. 2A). Also the relative positions and configurations of the various surgical devices 20a, 20b, 20c, as shown in FIG. 1, for example, may be displayed on display unit 80.

During a procedure involving insertion of a guidewire into a body lumen of a patient, for example, various endoscopic procedures, the guidewire shaft 22 may, unbeknownst to the surgeon, become looped. Looping of guidewire shaft 22 is undesirable, such that the surgeon should become aware of the looped configuration immediately. According to the present invention, the surgeon may visualize the configuration of guidewire shaft 22 in real time while guidewire shaft 22 is inserted in a patient's body. Such a procedure involving insertion of a guidewire into a body lumen of a patient may involve, for example, a guidable instrument such as a catheter or an endoscope, advancement of a dilator (e.g., surgical instrument 20b) via the guidewire, or placement of a stent (e.g., surgical instrument 20b) via the guidewire.

FIG. 2A schematically represents a guidewire 20a in a looped configuration, according to one embodiment of the invention. Guidewire 20a may include a guidewire shaft 22, having a guidewire distal end 22a and a guidewire proximal end 22b, and a guidewire handle 24 at proximal end 22b. Guidewire shaft 22, and in particular guidewire distal end 22a, may be steerable such that guidewire distal end 22a may be guided to a specific location within a body lumen or other part of a patient's body. Visualization of guidewire shaft 22 via display unit 80 may aid the surgeon's attempts to guide distal end 22a within the patient's body. Guidewire 20a may be electrically coupled to an electrical power source 40', which may provide electrical current to electromagnetic indicator coils 30. Guidewire 20a may include a plurality of electrical leads (not shown) for providing electrical current to each of the electromagnetic coils 30. Guidewire 20a may further include a switch 26 for controlling the flow of electrical current to electromagnetic coils 30.

FIG. 2B schematically represents a guidewire 20a in a curved configuration, also according to one embodiment of the invention. Guidewire 20a may include a guidewire shaft 22, having a guidewire distal end 22a and a guidewire proximal end 22b, and a guidewire handle 24 at proximal end 22b, generally as described with reference to FIG. 2A. Guidewire 20a may further include a battery 40", which may provide electrical current to electromagnetic indicator coils 30, and switch 26 for controlling the flow of electrical current to electromagnetic coils indicator 30.

FIG. 3 shows a portion of a guidewire shaft 22 including spaced apart coils 32a, 32b. Coils 32a, 32b may be spaced longitudinally along guidewire shaft 22. The shape or geometry of coils 32a, 32b, and their size relative to the size of guidewire shaft 22, may be other than that shown in FIG. 3. For example, FIG. 3 may not be drawn to scale. Although only two coils 32a, 32b are shown in FIG. 3, a larger number of coils may be used in accordance with embodiments of the invention. The number of coils and their spacing on guidewire shaft 22 may be, at least to some extent, a matter of design choice. Guidewire shaft 22 may have a diameter, D, typically in the range from about 0.02 to 0.08 inches, usually from about 0.025 to 0.07 inches, and often from about 0.03 to 0.05 inches.

Figure 4A:
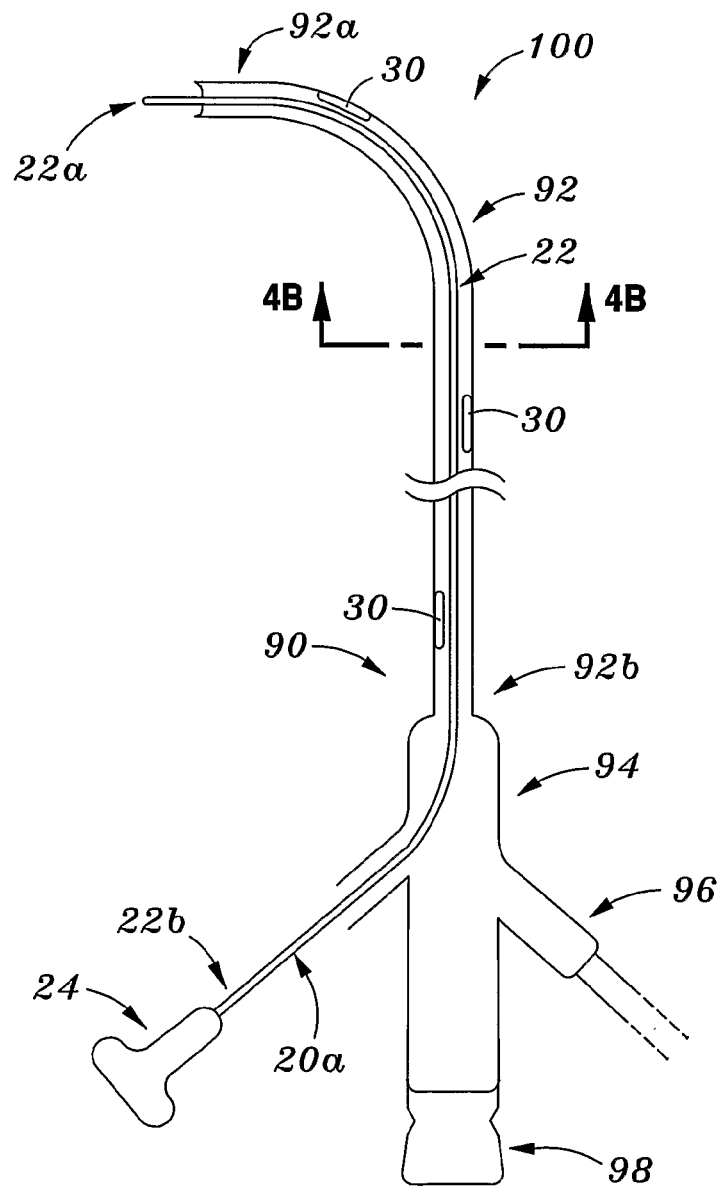
FIG. 4A schematic diagram of a guidewire system showing a guidewire in relation to a guidable device according to an embodiment of the present invention.

FIG. 4A schematically represents a guidewire system 100, which may include a guidewire 20a shown in relation to a guidable device 90. Guidable device 90 may be, for example, a catheter or an endoscope. Guidable device 90 may include a shaft 92, having a distal end 92a and a proximal end 92b, and a handle 94 at proximal end 92b. Guidewire system 100 may be used in conjunction with a monitoring unit 50 (see FIG. 1) for visualizing the configuration of guidewire shaft 22 in real time.

Figure 4B:
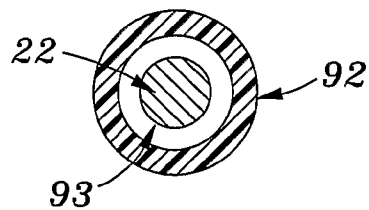
FIG. 4B is a sectional view taken along the line 4B-4B of FIG. 4A.

FIG. 4B shows a sectional view of shaft 92 taken along the line 4B-4B of FIG. 4A. Shaft 92 may have a lumen or working channel 93, which may extend the entire length of shaft 92. Lumen 93 may be capable of movably receiving guidewire shaft 22 so that guidewire shaft 22 may be advanced or retracted longitudinally relative to shaft 92 within lumen 93. Guidewire 20a of FIGS. 4A-4B may have elements and features as described with reference to FIGS. 1-3. In some embodiments, guidewire handle 24 may be removable from guidewire shaft 22, such that after advancing guidewire 20a into a specific location within a patient's body, guidewire handle 24 may be removed to allow guidable device 90 to be advanced along guidewire shaft 22. Guidable device 90 may further include a fitment 96, through which an ancillary device (not shown) may be passed via lumen 93. Ancillary devices may include, for example, forceps, dilators, fluid and vacuum lines, and the like. In embodiments where guidable device 90 may comprise an endoscope, an eyepiece 98 may be included, together with associated components, such as optical fibers, a light source, and the like.

In some embodiments, guidable device 90 may include a second set of electromagnetic indicator coils 30, whereby both guidable device 90 and guidewire shaft 22 may be visualized together on a display unit in the absence of fluoroscopy (exposure to X-rays), wherein an image of guidable device 90 may be distinguished from an image of guidewire shaft 22, for example, based on a color difference or line difference (e.g., a broken line versus a solid line).

Guidewire system 100 (FIGS. 4A-4B), guidewires 20a (FIGS. 2A-2B), and guidewire monitoring system 10 (FIG. 1) may provide greater flexibility of application and be more generally useful than technology that is limited only to endoscopes such as the ScopeGuide™ apparatus. For example, a guidewire 20a may be passed within the working channel of any flexible endoscope, and may be advanced distally beyond the endoscope in order to guide either advancement of the endoscope or advancement of another accessory device. As an example, during routine colonoscopy an acute angle may be encountered which does not allow the colonoscope to freely advance, in which event the physician may advance guidewire 20a through the working channel or lumen of the colonoscope beyond the acute angle while observing the configuration of guidewire 20a on display unit 80. A section of greater flexibility (e.g., less stiffness) near the distal end of the guidewire can aid in this maneuver. Thereafter, the colonoscope may be advanced over guidewire 20a by pushing the endoscope while holding the guidewire. A guidewire 20a of one embodiment may also be used in a similar manner during upper endoscopy, e.g., in situations where there is an alternated anatomy (e.g., Billroth operation II anastomosis).

Furthermore, guidewire 20a of the present invention may be used in conjunction with a surgical instrument 20b as shown in FIG. 1—such as a dilator (e.g., dilator 720 in FIG. 7)

which may itself include a plurality of electromagnetic indicator coils 30 to allow visualization of the surgical instrument 20b, (e.g., dilator 720) during a procedure. Still further, a surgical instrument 20b, which may be, for example, a jejunostomy tube (not shown), may be equipped with a plurality of electromagnetic coils 30 to allow visualization of the jejunostomy tube (surgical instrument 20b) during endoscopic placement of gastrojejunostomy.

Figure 5:
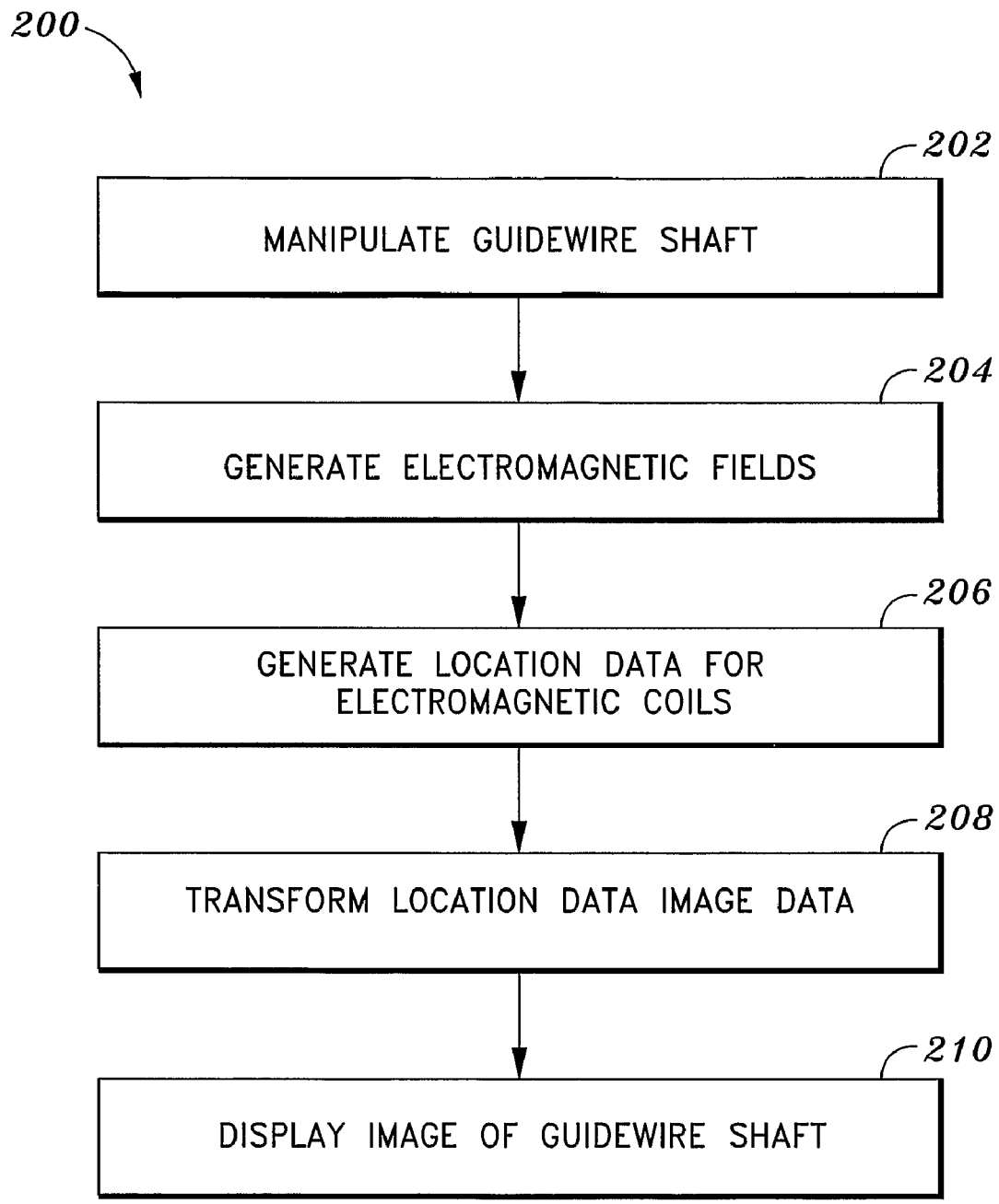
FIG. 5 is a flowchart for a method for monitoring guidewire shaft configuration, according to an embodiment of the present invention.

FIG. 5 schematically represents a series of steps involved in a method 200 for monitoring the configuration of a guidewire shaft and/or ancillary device (such as a stent, dilator, or jejunostomy tube, for example) in the absence of fluoroscopy, according to another embodiment of the invention, wherein step 202 may involve manipulating a guidewire shaft. As an example, step 202 may involve manipulating a guidewire shaft towards a specific location within a patient's body during a procedure. Alternatively, step 202 may involve manipulating a guidewire shaft during a training session for training an intern or trainee surgeon or other medical personnel. The guidewire shaft may be coupled to a guidewire handle, and the guidewire shaft may be steerable, e.g., within a body lumen, via the guidewire handle.

Step 202 may involve advancing the guidewire shaft through a working channel or lumen of an endoscope or catheter, wherein the endoscope or catheter is pre-positioned within a body lumen. As an example, the body lumen may be a blood vessel, a colon, a fallopian tube, and the like. Alternatively, step 202 may involve advancing the guidewire shaft through a body lumen to a specific location within the body lumen, wherein the guidewire serves to subsequently guide an endoscope or catheter over the guidewire shaft to the specific location within the body lumen, for example, according to the Seldinger technique. The guidewire shaft may include a plurality of electromagnetic coils spaced longitudinally along the guidewire shaft. In a further embodiment, step 202 may involve advancing an ancillary device, such as a dilator, stent, and the like, over the guidewire shaft, wherein the ancillary device may be equipped with a plurality of electromagnetic indicator coils 30 to allow visualization of the position and configuration of the ancillary device.

Step 204 may involve generating a plurality of electromagnetic fields corresponding to the plurality electromagnetic coils arranged on the guidewire shaft. The plurality of electromagnetic fields may be generated by passing an electric current through each of the plurality electromagnetic coils on the guidewire shaft.

Step 206 may involve generating or providing location data indicative of the relative location of each of the plurality of electromagnetic coils. The location data may be indicative of a direction and a distance from the detector (e.g., detector unit 60) of each of the corresponding plurality of electromagnetic fields generated by the plurality of electromagnetic coils. The location data may be provided via a detection unit or sensor for detecting the plurality of electromagnetic fields.

Step 208 may involve transforming the location data generated in step 206 into image-related data representing a configuration of the guidewire shaft. Step 208 may involve transforming the location data via a data processing unit. The location data generated in step 206 may be transformed into image-related data using a microprocessor or central processing unit (CPU), or a computer.

Thereafter, step 210 may involve displaying an image showing the configuration of the guidewire shaft. Step 210 may involve displaying the configuration of the guidewire shaft on a display unit, which may comprise a liquid crystal display (LCD), cathode ray tube (CRT), or TV monitor, and the like, whereby the surgeon or other member of the team may readily visualize the image of the guidewire shaft. As an example, by displaying an image showing the configuration of the guidewire shaft in step 210, the surgeon may immediately determine whether the guidewire shaft has adopted a looped (generally undesirable) configuration, thereby allowing measures to be taken to change (correct) the configuration of the guidewire shaft.

After the surgeon has visualized the configuration of the guidewire shaft, the guidewire shaft may again be manipulated (step 202), as appropriate, responsive to an observed guidewire shaft configuration (step 210).

Embodiments of the present invention may also be used with other devices, such as an ancillary device (e.g., surgical instrument 20b) that may be guided to a specific location (which may be marked, e.g., using indicator clips 20c) within a patient's body via a guidewire (e.g., guidewire 20a). For example, a device such as a dilator, a jejunostomy tube, or a stent may include a plurality of electromagnetic indicator coils 30 which may allow visualization of the dilator or stent on a display unit, e.g., as described with reference to FIGS. 1-5, in the absence of fluoroscopy. The guidewire may be a conventional guidewire or guidewire 20a according to an embodiment of the invention. In this way, a stent or other device may be placed in an occluded lumen or vessel without exposure to X-rays.

FIG. 7B shows one such possible example of a dilator 720 having embedded indicator coils 30 located, for example, toward a proximal end 724 of dilator 720 and toward a distal end 722 of dilator 720. Indicator coils 30 may be embedded in dilator 720, for example, by being integrally formed into the dilator 720 during its fabrication.

In an alternative embodiment, an indicator coil 30 of device indicator 700 may be provided with straps 734—as shown in FIG. 7A—for attachment to a device—such as dilator 720—or other surgical instrument 20b. Straps 734 may be provided with adhesive, for example; or may possess a combination of flexibility and stiffness that allows them to be deformed around a surgical instrument 20b yet retain a grip on instrument 20b; or an indicator coil 30 could be bonded to an instrument 20b with or without straps 734, for example. Device indicator 700 (as well as dilator 720 or other surgical instrument 20b) may be provided with a power source 40a. Power source 40a may include, for example, an antenna, a capacitive discharge device, or a battery. Power source 40a may be self-contained by the device indicator 700 or surgical instrument 20b (such as dilator 720) as shown in FIGS. 7A-7B. In an alternative embodiment, a power source 40b may be provided that is external and connected by wire 41 to the surgical instrument 20b or indicator clip 20c, as shown in FIG. 6B. It is desirable that the power sources 40a or 40b be capable of providing an electromagnetic field 31 detectable by detection unit 60 for about 1.0 hour.

FIG. 6A shows a clip fixing device 600 for placing an indicator clip 20c, for example, in the lumen of a body cavity of a patient. Clip fixing device 600 may include a handle 602 with a plunger 604. Activating plunger 604 may close fingers 606 (see also FIG. 6B) so that indicator clip 20c may be attached, for example, to a portion of tissue within a patient. Further activation of plunger 604 may separate indicator clip 20c from clip fixing device 600, allowing clip fixing device to be withdrawn, for example, from a patient. Clip fixing device 600 may have a shaft 608 adapted for guiding the indicator clip 20c to a desired location. Shaft 608 may include a plurality of electromagnetic indicator coils 30 which may be used for monitoring and guiding shaft 608 as in the case of guidewire 20a. Clip fixing device 600 may also be used in conjunction with guidewire 20a for monitoring the position and configuration of shaft 608 and indicator clip 20c. Indicator 20c may include one or more electromagnetic indicator coils 30, which may be fastened to or formed with the indicator clip 20c as described for the case of a device indicator 700. Indicator 20c may also include a power source 40a as described for the case of a device indicator 700.

Figure 8:
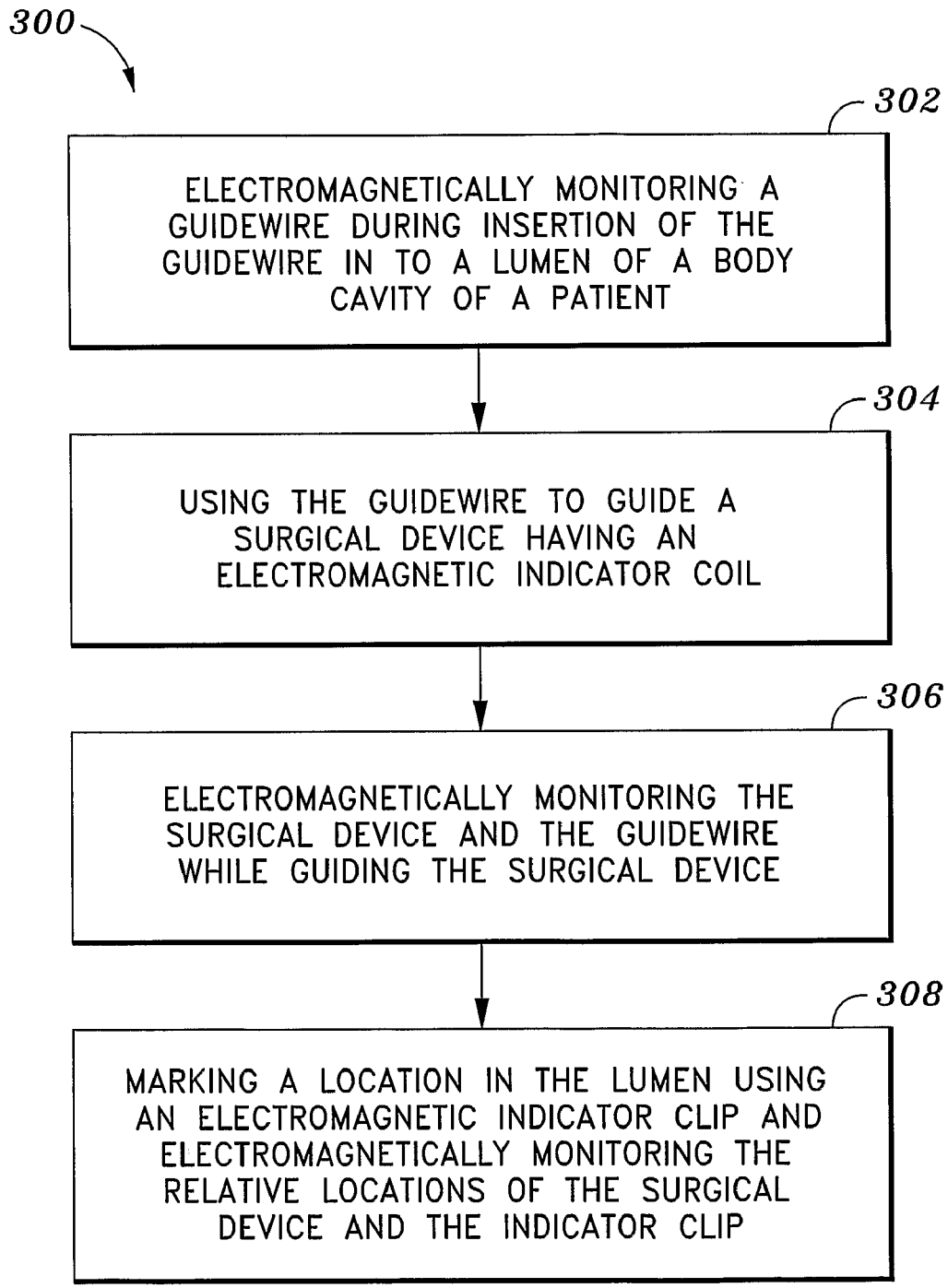
FIG. 8 is a flowchart for a method of positioning and monitoring the position and configuration of surgical instruments, according to one embodiment of the present invention.

FIG. 8 illustrates method 300 for fluoroscopy-free, electromagnetic monitoring and guiding of surgical implements including guidewires, device indicators, and indicator clips in accordance with embodiments of the present invention. Surgical method 300 may include a step 302 of electromagnetically monitoring a guidewire—such as guidewire 20a—during insertion of the guidewire into a lumen of a body cavity of a patient (not shown). Method 300 may include a step 304 of using the guidewire to guide a surgical device—including but not limited to stents, catheters, endoscopes, jejunostomy tubes, and dilators as well as other ancillary devices. In addition, step 304 may include guiding the shaft (e.g., shaft 608) of a clip fixing device—such as clip fixing device 600—through the lumen of a body cavity of a patient for attaching an indicator clip 20c as a location marker in the patient. The surgical device may have an electromagnetic indicator coil 30, such as illustrated by dilator 720. A device indicator 700 may be attached to a conventional surgical device to convert it to an electromagnetically monitorable surgical device—such as a surgical instrument 20b. Method 300 may include step 306, which may be accomplished simultaneously with the other steps, of electromagnetically monitoring the surgical device (e.g. surgical device 20, including guidewires 20a, surgical instruments 20b, and indicator clips 20c) and the guidewire while guiding the surgical device. Thus, a guidewire, a surgical instrument, and an indicator clip may all be electromagnetically monitored simultaneously in regard to location of each relative to the others and the overall configuration of each relative to the others.

For example, it may be desired to place dilator 720 in between two indicator clips 20c that have previously been placed as markers at proximal and distal ends of a restricted section of a body lumen. A guidewire 20a may be inserted until its distal end reaches the distal marker and the relative positions of the guidewire 20a and markers monitored. The dilator 720 may then be advanced until its distal end 722 reaches the proximal marker. The desired overall configuration of guidewire, dilator, and markers, however, is that the dilator 720 should be advanced along the guidewire 20a until the dilator 720 is situated between the proximal and distal markers with the distal end 722 near the distal marker and the proximal end 724 near the proximal marker. The surgeon can advance the dilator 720 along the guidewire 20a, electromagnetically monitoring the positions of all the devices relative to each other until the desired overall configuration of the guidewire 20a, dilator 720, and markers 20c is achieved. The guidewire 20a may then be removed.

Step 308 of method 300 includes the novel operation that one or more indicator clips—such as indicator clip 20c—can be placed at a selected location within a patient and its position monitored in conjunction with monitoring the position of another surgical device 20—such as surgical instrument dilator 720—to precisely position and monitor the location of the surgical device (e.g. dilator 720) relative to the position(s) and location(s) of the marker indicator clip or clips 20c.

It should be understood, of course, that the foregoing relates to exemplary embodiments of the invention and that modifications may be made without departing from the spirit and scope of the invention as set forth in the following claims.

I claim:

1. A system comprising:
 a guidewire having two or more electromagnetic indicator coils positioned thereon, including a first set and a second set of electromagnetic coils, the indicator coils configured to produce electromagnetic fields;
 a guidable surgical device having one or more of the electromagnetic indicator coils positioned thereon;
 a monitoring unit adapted to detect electromagnetic fields from said electromagnetic indicator coils;
 an indicator clip having a power source and being attached to the guidewire, wherein the indicator clip has one of the electromagnetic indicator coils positioned thereon;
 and a display unit configured to display the location and configurations of said guidewire and said guidable surgical device.

2. The system of claim 1, wherein said display unit displays the location of said indicator clip.

3. The system of claim 1 wherein said monitoring unit detects each corresponding electromagnetic field of the electromagnetic indicator coils individually to display the configuration of said surgical device and said guidewire.

4. The system of claim 1 further comprising:
 a plurality of indicator clips; and
 a plurality of instances of said guidable surgical device;
 the indicator clips and the guidable surgical devices having at least one of the electromagnetic indicator coils positioned thereon in addition to the indicator clips being positioned on the guidewire; and
 said display unit displays the location of said indicator clips and surgical instruments.

5. A guidewire system, comprising:
 a guidable device including an indicator clip having a plurality of fingers;
 a controller configured to close the plurality of fingers and to separate the indicator clip from the guidewire system;
 a guidewire attached to the guidable device, the guidewire including a guidewire shaft;
 a removable handle attached to the guidable device;
 electromagnetic coils positioned on the guidable device and spaced longitudinally on said guidewire shaft, said electromagnetic coils being adapted for generating a plurality of electromagnetic fields;
 a detection unit for generating location data indicative of a relative location of each of said electromagnetic coils;
 a data processing unit for transforming said location data into image data representing a configuration of said guidewire shaft; and
 a display unit for displaying an image representing said configuration of said guidewire shaft and an image of the guidable device so that the image of the guidable device is distinguishable from an image of guidewire shaft based on color difference.

6. The guidewire system of claim 5, wherein the guidable device is a catheter having a catheter lumen for movably receiving said guidewire shaft.

7. The guidewire system of claim 5, wherein the guidable device is an endoscope having an endoscope lumen for movably receiving said guidewire shaft.

8. The guidewire system of claim 5, wherein:
 said indicator clip includes at least one of the electromagnetic coils adapted for generating a plurality of electromagnetic field;
 said data processing unit also transforms said location data into image data representing a configuration of said indicator clip; and said display unit displays an image representing said configuration of said guidewire shaft and said indicator clip.

9. An instrument comprising:
a surgical instrument chosen from one of a dilator, a stent, a catheter, and a jejunostomy tube;
a plurality of electromagnetic coils including a first set and a second set of electromagnetic coils included in the surgical instrument, each of said plurality of electromagnetic coils being adapted for generating a corresponding one of a plurality of electromagnetic fields, and
said plurality of electromagnetic fields jointly defining a configuration of said surgical instrument, and
said plurality of electromagnetic coils being separable from said surgical instrument by a controller.

10. A method for monitoring a configuration of a guidewire and a guidable device, comprising:
generating electromagnetic fields from a plurality of electromagnetic coils spaced longitudinally along a shaft of the guidewire and from one or more of the electromagnetic coils positioned on the guidable device, wherein each of the electromagnetic coils is attached to a clip with a power source;
electromagnetically detecting said electromagnetic fields from the shaft and from the guidable device;
generating location data indicative of a relative location of each of said electromagnetic coils;
transforming said location data into image data representing a configuration of said guidewire shaft and the guidable device; and
via a display unit, displaying an image representing said configuration of said guidewire shaft and the guidable device so that the image of the guidable device is distinguishable from an image of the guidewire shaft;
wherein the image of the guidewire shaft and the image of the guidable device are distinguishable based on whether a broken line versus a solid line is used on the guidewire shaft and the guidable device.

11. The method of claim 10, wherein the image of the guidewire shaft and the image of the guidable device are distinguishable based on color.

12. The method of claim 10, wherein:
said image is based on said image data provided in said step (d); and
said location data provided in said step (c) is based on said electromagnetic detection provided in said step (b).

13. A surgical method comprising:
electromagnetically monitoring a guidewire during insertion of the guidewire into a lumen of a body cavity of a patient;
using the guidewire to guide a surgical device having an electromagnetic indicator coil; and
electromagnetically monitoring the surgical device and the guidewire while guiding the surgical device,
wherein electromagnetically monitoring includes producing electromagnetic fields within the patient with the guidewire including indicator coils positioned on the guidewire and the surgical device while displaying the guidewire and the surgical device to distinguish them by color, or by whether a broken line versus a solid line is used on the guidewire and the surgical device; and
placing an indicator clip having a power source and marking a location in the lumen of a patient using a plurality of the indicator coils.

14. The method of claim 13, further including:
electromagnetically monitoring the relative locations of the surgical device and the indicator clip.

* * * * *